US012558370B2

(12) United States Patent
Laver et al.

(10) Patent No.: US 12,558,370 B2
(45) **Date of Patent: *Feb. 24, 2026**

(54) INTACT PEA PROTEIN-BASED NUTRIENT COMPOSITION

(71) Applicant: Kate Farms, Inc., Santa Barbara, CA (US)

(72) Inventors: Richard Craig Laver, Park City, UT (US); Michelle Irene Laver, Park City, UT (US); Brett Holbrook Matthews, Santa Barbara, CA (US); William Bernard Pickar, Napa, CA (US); David Arthur Cole, Peoria, AZ (US); Steven Anthony Witherly, Valencia, CA (US); Caroline Hsin-Ai Witherly, Valencia, CA (US); Vanessa Laura Millovich, Carpinteria, CA (US); Christina Guerra Phreaner, Santa Barbara, CA (US)

(73) Assignee: Kate Farms, Inc., Goleta, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/006,793

(22) Filed: Jun. 12, 2018

(65) Prior Publication Data

US 2019/0374569 A1 Dec. 12, 2019

(51) Int. Cl.

| | |
|---|---|
| ***A61K 31/733*** | (2006.01) |
| ***A23J 3/14*** | (2006.01) |
| ***A23L 33/105*** | (2016.01) |
| ***A23L 33/12*** | (2016.01) |
| ***A23L 33/135*** | (2016.01) |
| ***A23L 33/15*** | (2016.01) |
| ***A23L 33/16*** | (2016.01) |
| ***A23L 33/185*** | (2016.01) |
| ***A23L 33/26*** | (2016.01) |
| ***A61K 31/202*** | (2006.01) |
| ***A61K 36/53*** | (2006.01) |
| ***A61K 36/898*** | (2006.01) |

(52) U.S. Cl.

CPC ............... *A61K 31/733* (2013.01); *A23J 3/14* (2013.01); *A23L 33/105* (2016.08); *A23L 33/12* (2016.08); *A23L 33/135* (2016.08); *A23L 33/15* (2016.08); *A23L 33/16* (2016.08); *A23L 33/185* (2016.08); *A23L 33/26* (2016.08); *A61K 31/202* (2013.01); *A61K 36/53* (2013.01); *A61K 36/898* (2013.01); *A23V 2002/00* (2013.01)

(58) Field of Classification Search

None

See application file for complete search history.

(56) References Cited

U.S. PATENT DOCUMENTS

| | | | | |
|---|---|---|---|---|
| 3,030,955 | A | 4/1962 | Gossett et al. | |
| 3,642,047 | A | 2/1972 | Waage | |
| 4,326,574 | A | 4/1982 | Pallaroni et al. | |
| 4,542,530 | A | 9/1985 | Thomas et al. | |
| 4,578,074 | A | 3/1986 | van Leerdam | |
| 4,840,017 | A | 6/1989 | Miller et al. | |
| 4,869,725 | A | 9/1989 | Schneider et al. | |
| 5,137,527 | A | 8/1992 | Miller et al. | |
| 5,424,034 | A | 6/1995 | Hilmersson | |
| 5,629,023 | A | 5/1997 | Bland | |
| 5,728,678 | A | 3/1998 | Trimbo et al. | |
| 6,039,718 | A | 3/2000 | Niedospial, Jr. | |
| 6,277,092 | B1 | 8/2001 | Cole et al. | |
| 6,989,161 | B2 | 1/2006 | Roufs et al. | |
| 7,875,291 | B1 * | 1/2011 | Habib .................... | A23L 33/30 424/451 |
| 7,950,547 | B2 | 5/2011 | Saunders et al. | |
| 8,007,174 | B2 | 8/2011 | Yamaguchi et al. | |
| 8,056,510 | B2 | 11/2011 | Handley et al. | |
| 9,687,012 | B2 | 6/2017 | Kesler et al. | |
| 9,801,814 | B2 | 10/2017 | Mager et al. | |
| 9,925,120 | B2 | 3/2018 | Kropczynski et al. | |
| 10,806,169 | B2 | 10/2020 | Laver et al. | |
| 11,547,629 | B2 | 1/2023 | Phreaner | |
| 2003/0104033 | A1 | 6/2003 | Lai et al. | |
| 2006/0282061 | A1 | 12/2006 | Domkowski et al. | |

(Continued)

FOREIGN PATENT DOCUMENTS

| | | | |
|---|---|---|---|
| AU | 2007340638 | B2 | 11/2010 |
| AU | 2017225011 | A1 * | 9/2017 |

(Continued)

OTHER PUBLICATIONS

Machine translation of CN102669398A (Year: 2012).*

Muanda, F., et al. "Phytochemical Composition and Antioxidant Capacity of Three Malian Medicinal Plant Parts," Evidence-Based Complementary and Alternative Medicine, 2011, Article ID 674320, 1-8 (2008).

Clinical Trial NCT01298154: Effects of Intact and Hydrolyzed Pea Protein on Food Intake, Glycemic Response and Subjective Appetite http://sunrisechildrenshospital.com/hl/?/21527/Branched-Chain-Amino-Acids-BCAAs-.

Anonymous, "Agave Inulin: All You Need to Know," 1-4 (2016).

Gunnars, K., "How to Optimize Your Omega-6 to Omega-3 Ratio," Jun. 11, 2018 (Jun. 11, 2018); p. 7-9, Section Entitled "Avoid Vegetable Oils High In Omega-6." https://www.healthline.com/nutrition/optimize-omega-6-omega-3-ratio.

(Continued)

*Primary Examiner* — Terry A Mckelvey

(74) *Attorney, Agent, or Firm* — Wilson Sonsini Goodrich & Rosati

(57) ABSTRACT

The present invention discloses a nutritional composition and method of using and making the nutritional composition. The nutritional composition is an intact pea protein based nutrient composition for use in both enteral and oral feeding, and provides a non-allergenic diet for providing optimal nutrition to users. The nutritional composition is made from organic and plant-based ingredients. The nutritional composition has pea protein, phytochemical extracts, fatty acids, organic ingredients free of the top eight allergens and corn, and prebiotic fiber. The nutritional composition is provided in liquid form for enteral and/or oral feeding.

38 Claims, 1 Drawing Sheet

(56) References Cited

U.S. PATENT DOCUMENTS

2007/0014909 A1 1/2007 Mai et al.
2007/0042992 A1 2/2007 Frippiat et al.
2007/0148305 A1 6/2007 Sherwood et al.
2007/0224323 A1 9/2007 Goldman
2009/0087519 A1 4/2009 Hundscheid et al.
2009/0124685 A1 5/2009 Uribe et al.
2009/0304823 A1 12/2009 Elizabth et al.
2010/0124592 A1 5/2010 Anderson
2010/0184963 A1 7/2010 Scanlin et al.
2010/0239712 A1 9/2010 Brooks et al.
2010/0249728 A1 9/2010 Kobashi et al.
2011/0021421 A1 1/2011 Kiers et al.
2011/0206787 A1 8/2011 West et al.
2011/0257089 A1 10/2011 Huisman et al.
2012/0040014 A1 2/2012 Settineri et al.
2012/0100257 A1 4/2012 Lambach et al.
2013/0023468 A1 1/2013 Hofman et al.
2013/0102990 A1 4/2013 Domkowski et al.
2013/0115329 A1 5/2013 Savant et al.
2013/0203663 A1 8/2013 Mager et al.
2013/0210715 A1 8/2013 Greenberg et al.
2013/0243904 A1 9/2013 Cordle et al.
2013/0261183 A1* 10/2013 Bhagat .................. G16H 20/60 426/71
2014/0113031 A1 4/2014 Lee
2014/0154364 A1* 6/2014 Cotton .................... A23L 19/09 426/302
2014/0335252 A1 11/2014 Arcieri
2015/0164985 A1 6/2015 Claudia et al.
2015/0305359 A1 10/2015 Ao et al.
2015/0342237 A1 12/2015 Daikeler et al.
2016/0051444 A1 2/2016 Muth
2016/0113987 A1* 4/2016 Choi .................. A61K 2300/00 424/439
2016/0278415 A1 9/2016 Marsland
2016/0316810 A1 11/2016 Terp et al.
2018/0015032 A1* 1/2018 LeBrun-Blashka .......................... A61K 9/0095
2019/0021387 A1* 1/2019 Barata ..................... A23J 3/346
2019/0350245 A1 11/2019 Laver et al.
2020/0077691 A1* 3/2020 Dewille ................ A23L 33/125
2020/0188455 A1 6/2020 Mager et al.
2021/0045423 A1 2/2021 Laver et al.
2021/0401021 A1 12/2021 Laver et al.
2022/0030909 A1 2/2022 Laver et al.
2023/0132388 A9 4/2023 Laver et al.
2023/0136482 A1 5/2023 Vernacchia et al.
2023/0140497 A1 5/2023 Bailey et al.

FOREIGN PATENT DOCUMENTS

CN 1400869 A 3/2003
CN 101175408 A 5/2008
CN 102271525 A 12/2011
CN 102669398 A * 9/2012
CN 103025178 A 4/2013
CN 103153095 A 6/2013
CN 104322639 A * 2/2015
CN 105285023 A * 2/2016
CN 105533720 A * 5/2016
CN 105960173 A 9/2016
CN 106962598 A * 7/2017
CN 107259586 A * 10/2017
CN 107684561 A * 2/2018
CN 107692221 A * 2/2018
CN 107997173 A * 5/2018
EP 2880996 A1 * 6/2015
EP 1 972 346 10/2015
EP 3973792 A1 3/2022
JP 2008/206479 9/2008
JP 2014505702 A 3/2014
JP 3193095 U * 9/2014
JP 2017531429 A 10/2017
JP 2019503195 A 2/2019
JP 2021524755 A 9/2021
WO WO-2005089697 A1 9/2005
WO WO 2007063142 6/2007
WO WO2010126362 A1 * 11/2010
WO WO 2012027287 3/2012
WO WO2013138906 A1 * 9/2013
WO 2013148685 10/2013
WO WO2013148685 A1 * 10/2013
WO WO 2017095897 6/2017
WO WO 2017129921 A1 8/2017
WO WO 2019075307 A1 4/2019
WO WO 2019222000 A1 11/2019
WO WO-2019240943 A1 12/2019
WO WO-2021160656 A1 8/2021
WO WO-2023076572 A1 5/2023

OTHER PUBLICATIONS

International Search Report and Written Opinion of the International Searching Authority, mailed on Sep. 11, 2019, from International Application No. PCT/US19/31362, filed on May 8, 2019. 11 pages.

International Search Report and Written Opinion of the International Searching Authority, mailed on Sep. 17, 2019, from International Application No. PCT/US19/34236, filed on May 29, 2019. 10 pages.

Johnson, J.J., “Carnosol: A Promising Anti-Cancer and Anti-Inflammatory Agent,” Cancer Letters, 305(1): 1-7 (2011).

Nemzer, B.V., et al., New Insights on Effects of a Dietary Supplement on Oxidative and Nitrosative Stress on Humans, Food Science & Nutrition, 2(6): 828-839 (2014). https://www.ncbi.nlm.nih.gov/pmc/articles/PMC4256589.

Nsa, “Sunflower Oil” National Sunflower Association, Oct. 8, 2010 (Oct. 8, 2010); entire document. https://web.archive.org/web/20101008154453/https://www.sunflowernsa.com /oil/Linoleic-Sunflower-Oil/.

Phillips, E.M., et al., “Peptide-Based Formulas: The Nutraceuticals of Enteral Feeding?,” EPCN, 40-45: (2005).

Textron, “Sunflower Oil, Organic” Textran Product Data Sheet, Dec. 31, 2007 (Dec. 31, 2007); p. 1. https://www.brenntag.com/media/documents/bsi/product_data_sheets/life_science/textron_natural_oils/sunflower_oil_refined-tx008081_pds.pdf.

Wikipedia, “Dietary fiber”, Nov. 30, 2017 (Nov. 30, 2017), retrieved on Jul. 8, 2019 from 1-19 https://en.wikipedia.org/w/index.php?title=Dietary_fiber&oldid=812822101; entire document, especially p. 6 para 4.

International Preliminary Report on Patentability, mailed on Dec. 24, 2020, from International Application No. PCT/US19/034236, filed on May 29, 2019. 9 pages.

International Preliminary Report on Patentability, mailed on Nov. 26, 2020, from International Application No. PCT/US2019/031362, filed on May 8, 2019. 9 pages.

Bailey, M. et al., “Weight Gain in Oncology Patients Using a Plant-Based Oral Nutrition Supplement,” *Clinical Nutrition ESPEN*, 40:661 (2020).

Cohen, S. et al., “Improved GI Tolerance and Weight Gain in Pediatric Patients Using Plant-Based Enteral Formulas,” *Journal of Parenteral and Enteral Nutrition*, 44(3): 274 (2020).

Cohen, S. et al., “Patient-Reported Outcomes Indicate Plant-Based Enteral Formula Improves Nutrition and Gastrointestinal Symptoms,” *Journal of Parenteral and Enteral Nutrition*, 44 (3): 275 (2020).

Cohen, S. et al., “Patient-Reported Outcomes of GI Symptoms and Adherence Among Pediatric Patients Using a Pea Protein Plant-Based Enteral Formula,” *JPGN*, S454-456 (2020).

Anonymous, “PURE. Manufacturer of Hypoallergenic Nutritional Supplements,” URL:https://www.pureencapsulationspro.com/media/PLs/2017 PL_ Catalog_Price_web.pdf (2017).

Supplementary European Search Report, mailed on Jan. 13, 2022, from European Patent Application No. 19 80 4397, filed on May 8, 2019. 3 pages.

(56) References Cited

OTHER PUBLICATIONS

Supplementary European Search Report, completed on Jan. 12, 2022, from European Patent Application No. 19 81 9010, filed on May 29, 2019. 2 pages.
Aluko, R.E., "Determination of Nutritional and Bioactive Properties of Peptides in Enzymatic Pea, Chickpea, and Mung Bean Protein Hydrolysates," *Journal of AOAC International*, 9(4): 947-956 (2008).
Boehm, A. et al., "Heat-induced degradation of inulin," *Eur Food Res Technol*, 220: 466-471 (2005).
Chakrabarti, S. et al., "Bioactive peptides on endothelial function," *Food Science and Human Wellness*, 5: 1-7 (2016).
Chakrabarti, S. et al., "Food-Derived Bioactive Peptides on Inflammation and Oxidative Stress," *Hindawi Publishing Corporation, BioMed Research International*, Article ID 608979: 1-11 (2014).
Chalamaiah, M. et al., "Immunomodulatory and anticancer protein hydrolysates (peptides) from food proteins: A review," *Food Chemistry*, 245: 205-222 (2018).
Corrochano, A.R. et al., "Intestinal health benefits of bovine whey proteins after simulated gastrointestinal digestion," *Journal of Functional Foods*, 49: 526-535 (2018).
Corrochano, A.R. et al., "Invited review: Whey proteins as antioxidants and promoters of cellular antioxidant pathways," *J. Dairy Sci.*, 101: 4747-4761 (2017).
Feng, J. et al., "Maillard reaction products as functional components in oil-in-water emulsions: A review highlighting interfacial and antioxidant properties," *Trends in Food Science & Technology*, 121: 129-141 (2022).
Gilmartin, S. et al., "Whey for Sarcopenia; Can Whey Peptides, Hydrolysates or Proteins Play a Beneficial Role?," *Foods*, 9(750): 1-25 (2020).
Girgih, A.T. et al., "Preventive and treatment effects of a hemp seed (*Cannabis sativa* L.) meal protein hydrolysate against high blood pressure in spontaneously hypertensive rats," *Eur J Nutr*, DOI 10.1007/s00394-013-0625-4 (2013). 10 pages.
Jiang, W. et al., "Impact of pea protein-inulin conjugates prepared via the Maillard reaction using a combination of ultrasound and pH-shift treatments on physical and oxidative stability of algae oil emulsions," *Food Research International*, 156: 1-14 (2022) 111161.
Kutzli, I. et al., "Glycation of Plant Proteins Via Maillard Reaction: Reaction Chemistry, Technofunctional Properties, and Potential Food Application," *Foods*, 10(376): 1-40 (2021).
Li, H. et al., "Blood Pressure Lowering Effect of a Pea Protein Hydrolysate in Hypertensive Rats and Humans," *Journal of Agricultural and Food Chemistry*, 59: 9854-9860 (2011).
Li, S. et al., "Molecular targets and mechanisms of bioactive peptides against metabolic syndromes," *Food & Function*, DOI: 10.1039/c7fo01323j (2017). 11 pages.
Luna-Vital, D. et al., "Peptides from legumes with antigastrointestinal cancer potential: current evidence for their molecular mechanisms," Accepted Manuscript, *Food Science*, (2018). 19 pages.
Malomo, S.A. et al., "Structural and Antihypertensive Properties of Enzymatic Hemp Seed Protein Hydrolysates," *Nutrients*, 7: 7616-7632 (2015).
Mancilla-Margalli, N.A. et al., "Generation of Maillard Compounds from Inulin during the Thermal Processing of *Agave tequilana* Weber Var. *azul*," *J. Agric. Food Chem.*, 50: 806-812 (2002).
Martínez-Maqueda, D et al., "Antihypertensive peptides from food proteins: a review," *Food & Function*, 3: 350-361 (2012).
Mojica, L. et al., "Evaluation of the hypoglycemic potential of a black bean hydrolyzed protein isolate and its pure peptides using in silico, in vitro and in vivo approaches," *Journal of Functional Foods*, 31: 274-286 (2017).
Mojica, L. et al., "Optimization of enzymatic production of anti-diabetic peptides from black bean (*Phaseolus vulgaris* L.) proteins, their characterization and biological potential," *Food & Function*, 7: 713-727 (2016).
Real Hernandez, L.M. et al., "Enzymatic Production, Bioactivity, and Bitterness of Chickpea (*Cicer arietinum*) Peptides," *Comprehensive Reviews in Food Science and Food Safety*, 0: 1-34 (2019).
Shaw, K.A., et al., "The Feasibility of a Pea Protein Supplement with High Iron Bioavailability for Female Runners: A Randomized Control Trial," *Research Square*, 1-20 (2022).
Udenigwe, C.C. et al., "Food Protein-Derived Bioactive Peptides: Production, Processing, and Potential Health Benefits," *Journal of Food Science*, 71(1): R11-R24 (2012).
Vermeirssen, V. et al., "Optimisation and validation of an angiotensin-converting enzyme inhibition assay for the screening of bioactive peptides," *J. Biochem. Biophys. Methods*, 51: 75-87 (2002).
Xu, Q. et al., "Bioavailability of bioactive peptides derived from food proteins across the intestinal epithelial membrane: A review," *Trends in Food Science & Technology*, 86: 399-411 (2019).
Zha, F. et al., Conjugation of Pea Protein Isolate via Maillard-Driven Chemistry with Saccharide of Diverse Molecular Mass: Molecular Interactions Leading to Aggregation or Glycation, *J. Agric. Food Chem.*, 68: 10157-10166 (2020).
Zhang, Z. et al., "Maillard reaction between pea protein isolate and maltodextrin via wet-heating route for emulsion stabilisation," *Future Foods*, 6: 1-10 (2022) 100193.
Moore, C., "Kate Farms Launches Core Essentials Peptide Tube Feeding Formula for CF, Other Conditions", Cystic Fibrosis News Today, Aug. 15, 2017, pp. 6.
Nemzer, B.V., et al., "New insights on effects of a dietary supplement on oxidative and nitrosative stress in humans", Food Science & Nutrition, 2(6), 828-839, (2014).
Andrea, M. et al., "Fruit Syrups: Sweet Concentrated Sources", The World of Food Ingredients, Mar. 2016, pp. 44-46 (Year: 2016).
Anonymous: "Vanilla Bliss Meal Replacement Shake", Mintel; Jun. 17, 2014. 4 Pages.
Kate Farms Shakes: Komplete, Peptide 1.0 and Peptide 1.5. Vegan and Hypoallergenic Complete Nutrition Meal Replacement Protein Shakes (Corn free, Soy free, Wheat free, Dairy free)., Jan. 11, 2017(online), pp. 1-6, retrieved on Jan. 4, 2024, retrieved from the internet https://www.ladyoflyme.com/features/katefarms.
Nemzer, B., et al., "Decrease of Free Radical Concentrations in Humans Following Consumption of a High Antioxidant Capacity Natural Product," Food Science & Nutrition, 2(6): 647-654 (2014).
Alexander, J. W. et al., "Role of Arginine and Omega-3 Fatty Acids in Wound Healing and Infection", Advances in Wound Care, 2014, vol. 3, No. 11, pp. 682-690.
Alvirdizadeh, S., et al., "A Prospective Study on Total Protein, Plant Protein and Animal Protein in Relation to the Risk of Incident Chronic Kidney Disease," BMC Nephrology, 21: 1-7 (2020).
Anonymous, "Enteral Feeding Systems—Design and Testing," International Standard, 1-44 (2020).
Anonymous, "Frequently Asked Questions About Medical Foods; Second Edition," U. S. Department of Health and Human Services, 1-12 (2016).
Carrero, J.J., et al., "Plant-Based Diets to Manage the Risks and Complications of Chronic Kidney Disease, " Nature Reviews, 16: 525-542 (2020).
Cases, A., et al., "Vegetable-Based Diets for Chronic Kidney Disease? It is Time to Reconsider," Nutrients, 11(1263): 1-26 (2019).
Chen, X., et al., "The Association of Plant Protein Intake with All-Cause Mortality in CKD," Am. J. Kidney Dis., 67(3): 423-430 (2016).
Julson, E., "Pea Protein Powder: Nutrition, Benefits and Side Effects", Nov. 30, 2018, downloaded on Mar. 23, 2023 from https://web.archive.org/web/20181130212649/www.healthline.com/nutrition/pea-protein-powder (Julson). (Year: 2018).
Kate Farms Komplete Vanilla Meal Replacement Shake, Gluten Free, NutFree, Dairy Free, Organic Plant Protein Ready to Drink Case of 12, amazon.sg, Mar. 1, 2017 (online), pp. 1-6 and retrieved on Sep. 29, 2023, retrieved from the internet https://www.amazon.sg/Kate-Farms-Komplete-Vanilla-Replacement/dp/B06XNPQ83T.
Ojo, O. et al., "The Effect of Dietary Glycaemic Index on Glycaemia in Patients with Type 2 Diabetes: A Systematic Review and Meta-Analysis of Randomized Controlled Trials", Nutrients, 2018, vol. 10, No. 373, pp. 1-15.
Shah, A.P., et al., "Is There a Role for Ketoacid Supplements in the Management of CKD?," Am. J. Kidney Dis., 65(5): 659-673 (2015).

(56) References Cited

OTHER PUBLICATIONS

Pure Encapsulations, 'Manufacturer of Hypoallergenic Nutritional Supplements. 2017 Professional Product List', [retrieved from the Internet Feb. 6, 2024] URL:https://www.pureencapsulationspro.com/media/PLs/2017_PL_Catalog_Price_web.pdf, Published Mar. 6, 2017.
Singletary, K.W., "Vanilla Potential Health Benefits," Nutrition Today, 55(4): 186-196 (2020).
Mager, D. R. et al. (2003). Branched chain amino acid requirements in School-Aged children determined by Indicator Amino acid oxidation (IAAO). J. Nutr. 133, No. 11, 3540-3545.
Overdiun, J., et al. (2015). Nutralys® pea protein: characterization of in vitro gastric digestion and in vivo gastrointestinal peptide responses relevant to satiety. Food & Nutrition Research, 59: 25622.
Calder, P. C. (2013). Omega-3 polyunsaturated fatty acids and inflammatory processes: nutrition or pharmacology?. British journal of clinical pharmacology, 75(3), 645-662.
Maroon, J.C. & Bost, J. W. (2006). Ω-3 Fatty acids (fish oil) as an anti-inflammatory: an alternative to nonsteroidal anti-inflammatory drugs for discogenic pain. Surgical Neurology, 65(4), 326-331.
Nicholson LJ (2011), Acute pancreatitis: should we use antibiotics? Curr Gastroenterol Rep. Aug;13(4):336-43.
Shyamala, B. N., Madhava, Naidu M., Sulochamma G. and Srinivas, P. (2007), Studies on the Antioxidant Activities of Natural Vanilla Extract and Its Constituent Compounds through in Vitro Models, Journal of Agric. Food Chem., 55 (19), pp. 7738-7743.
Hannah D. Holschery, (2017). Dietary Fiber and Prebiotics and the Gastrointestinal Microbiota. Gut Microbes, vol. 8, No. 2, 172-184.
Holsher, H. D., Bauer, L. L., Gourineni, V., Pelkman, C. L., Fahey Jr, G. C., & Swanson, K. S. (2015). Agave Inulin Supplementation Affects the Fecal Microbiota of Healthy Adults Participating in a Randomized, Double-Blind, Placebo-Controlled, Crossover Trial-3. The Journal of nutrition, 145(9), 2025-2032.
Clinical Trial NCT01298154: Effects of Intact and Hydrolyzed Pea Protein on Food Intake, Glycemic Response and Subjective Appetite http://sunrisechildrenshospital.com/hl/?/21527/Branched-Chain-Amino-Acids-BCAAs-, 2011.
Ghani Khan, Mohammad Najmul. Safoof-e Matar Bara-e Zaheer. Traditional Knowledge Resource JA6/709D. Sheikh Mohd Basheer & Sons, Lahore. 2 pages (1926).
Ibn-E-Sina, Abu Ali. Dawa-e-Karasna, Traditional Knowledge Resource AH1/599B. Institute of History of Medicine and Medical Research, Jamia Hamdard, New Delhi. 2 pages (1987).
Kaiyadevanighantau, Kaiyadeva. Tulasi. Traditional Knowledge Resource RS6/523. 1st Edn., Chaukhambha Orientalia, Varanasi. 3 pages (1979).
Ketterling, Alexa. What Are the Different Types of Sunflower Oil. Centra Foods, Simply Authentic. 10 pages (2020). Available at https://www.centrafoods.com/blog/what-are-the-different-types-of-sunflower-oil.
Khan, Mohammad Shareef. Dawa Bara-e-Zaheer. Traditional Knowledge Resource MH1/2618. Afzal-al-Matabe, Barqi Press, Delhi. 2 pages (1921).
Krishan, Gopal. Rasonakarpura Vati. Traditional Knowledge Resource RS21/173. 8th Edn., Krishan Gopal Ayurveda Bhawan. 3 pages (1990).
Beverage Industry, Komplete Ultimate Meal Replacement Shakes, 2013. Available at URL:https://www.bevindustry.com/articles/86635-komplete-ultimate-meal-replacement-shakes pp. 1-5.
Grubiak, Katie. How to Choose a Supplemental Nutrition Shake, Eating Disorder Therapy LA, Mar. 5, 2018; [retrieved on Apr. 16, 2025]. Available at URL:https://www.eatingdisordertherapyla.com/how-to-choose-a-supplemental-nutrition-shake/ pp. 1-15.
Singletary, Keith. Rosemary: an overview of potential health benefits. Nutrition Today 51(2):102-112 (2016).

* cited by examiner

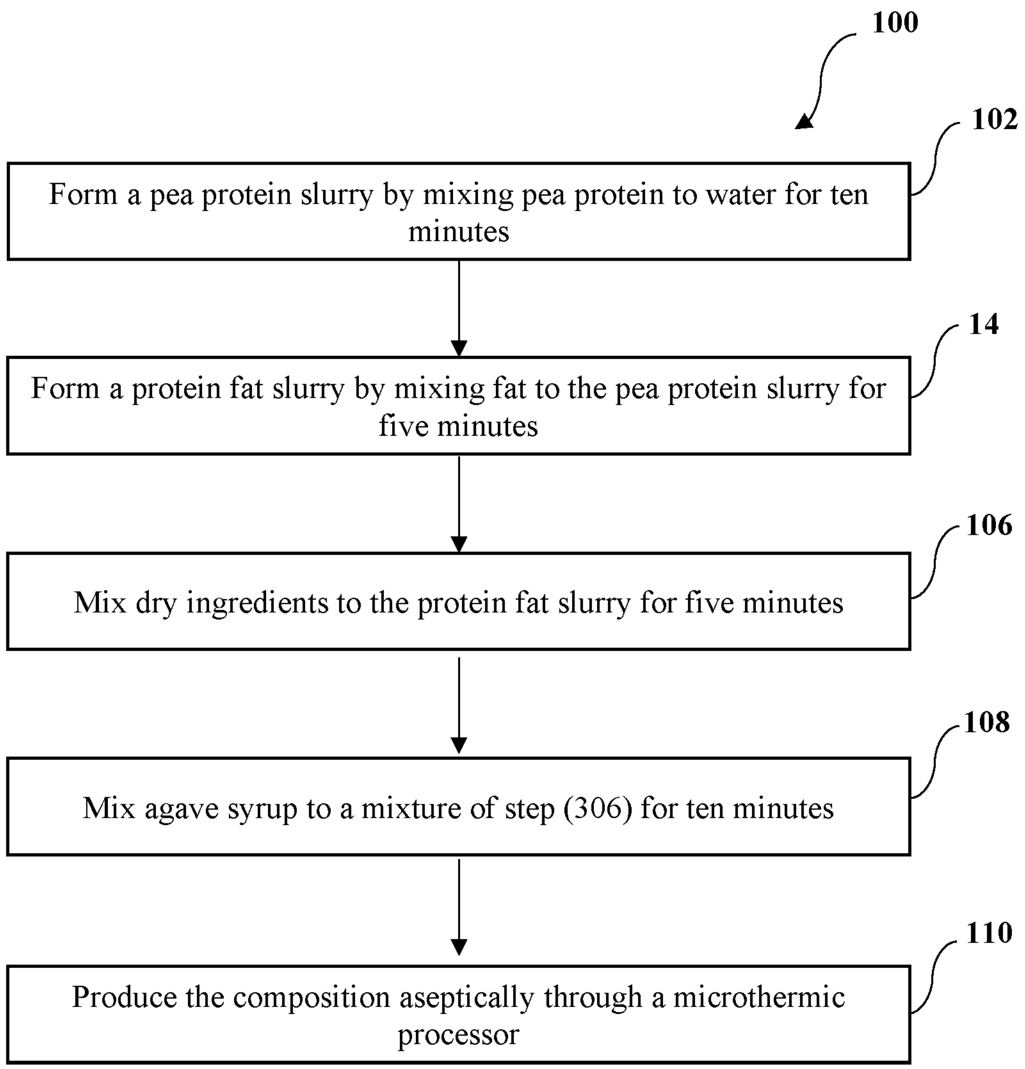
100
102
Form a pea protein slurry by mixing pea protein to water for ten minutes
14
Form a protein fat slurry by mixing fat to the pea protein slurry for five minutes
106
Mix dry ingredients to the protein fat slurry for five minutes
108
Mix agave syrup to a mixture of step (306) for ten minutes
110
Produce the composition aseptically through a microthermic processor

INTACT PEA PROTEIN-BASED NUTRIENT COMPOSITION

FIELD OF THE INVENTION

The present invention generally relates to nutrition and the healthcare field. More specifically, the present invention relates to a natural and non-allergenic pea protein based nutrient composition for use in both enteral and oral feeding.

BACKGROUND OF THE INVENTION

Liquid nutrition supplements are well-known and have been readily available in stores and for medical purposes for many years. These compositions come in various flavors and can be can be consumed in addition to a regular diet, as a replacement for meals in a day, or in lieu of food altogether. Initially, they were developed mostly for use with medical supervision by the elderly, patients recovering from illness, and others who need help putting on or retaining weight, but more have recently been marketed for use by healthy adults.

In the medical field, these compositions are used to treat patients with a variety of ailments that have difficulty digesting foods and have decreased nutrient intake caused by, for example: gastroesophageal reflux, or rumination; malabsorption due to disorders such as short bowel syndrome, jejunostomy, EOE (eosinophilic esophagitis), celiac disease, cystic fibrosis, Crohn's Disease or disaccharidase deficiency; endocrine dysfunction resulting from conditions such as diabetes mellitus and proteinuria; increased energy requirements of diseases such as bronchopulmonary dysplasia, cystic fibrosis, or hyperthyroidism; and increased energy needs due to trauma, post-operative recovery, nutritional treatment before, during and after cancer treatment, and during times of metabolic stress as seen with neurological disorders such as cerebral palsy and amyotrophic lateral sclerosis (ALS). The above may be characterized generally as Failure to Thrive ("FTT"). Approximately 3-5% of all children admitted to tertiary care centers, and 1% of all children admitted to any hospital, are diagnosed with above ailments or the like.

Pediatric and infant manufactured nutritional liquids and powders comprising a targeted selection of nutritional ingredients are well known and widely available, some of which may provide a sole source of nutrition, while others may provide a supplemental source. Some of these nutritional liquids utilize pea protein as its main source of protein.

For example, WO 2013148685 to Neal et al describes a nutritional composition including an intact pea protein concentrate as a sole protein source in the nutritional composition because intact pea protein imparts a number of important benefits to the nutritional compositions including excellent texture, sweetness and a smooth and creamy mouthfeel, as well as beneficial effects on glycemic control and response and glucose modulation.

Another example is EP 1 972 346 (WO2007/063142) which discloses a pea-based protein mixture comprising 50 weight % caseinate, 25 weight % whey proteins and 25 weight % pea proteins.

However, these examples disclose the use of intact proteins, do not contemplate the use of pea protein together with other organic plant-based ingredients for patients with impaired gastrointestinal absorption and digestion, are generally whole-food based, nor are they free of common food allergens.

Indeed, food allergies in children are very common-almost 8% of children in the United States have some type of food allergy. Common allergens consist of milk (including whey, casein, and lactose), wheat, soybeans, eggs, peanuts, tree nuts, fish, shellfish, and corn. As nutrients are necessary for proper growth and development, removing them from a regular diet leads to malnutrition issues. In particular, removal of milks and/or milk proteins, eggs, and soybeans from the diets of children in growth stages presents a serious problem from the perspective of dietetics. Currently, products in markets utilize corn sweeteners, corn starches, synthetic corn derivatives and corn oils, many of which are produced from genetically modified sources. In addition, these products utilize the protein of milk, whey or casein making their products unavailable to those patients with galactosemia, who are lactose intolerant or have a milk allergy.

Furthermore, conventional liquid nutrition formulas do not contain these optimal levels of fatty acids, are often found to have an unfavorable medium chain triglycerides (MCT) to long chain triglycerides (LCT) ratio, and no source of omega 3 fatty acids. Moreover, some of the products are made of synthetic and artificial ingredients. These compositions provide unpleasant taste and odors, preventing them from being taken by patients for a prolonged period, even though they may theoretically be free from allergens.

In light of the above-mentioned problems, there is a need for a product that addresses the issues faced by people and patients who rely upon a plant-based, vegan formula free of common allergens and synthetic ingredients which are currently not found in the market. Further, there is a need for a plant-based composition comprising phytonutrients, beneficial fats, and fibers, that are suitable for both oral and enteral administration.

SUMMARY OF THE INVENTION

The present invention discloses a nutritional composition and method of using and making the nutritional composition. The nutritional composition is a composition free of allergens for providing optimal nutrition to users. The nutritional composition is a plant-based, vegan formula free of common allergens and synthetic ingredients. The composition is based on a pea protein composition for use in both enteral and oral feeding.

According to the present invention, the nutritional composition constitutes organic and plant-based ingredients. In an embodiment, the nutritional composition comprises at least one of a protein source, one or more phytochemical extracts, one or more fatty acids, one or more organic ingredients free of common allergens (e.g., the top eight allergens) and corn, and one or more prebiotic fibers. In one embodiment, the protein source is pea protein. In one embodiment, the phytochemical extracts are a blend of fruits, vegetables, herbs and spices. In another embodiment, the phytochemical extracts comprise one or more combinations of a blend of phytochemical extracts from fruits, vegetables, herbs, and spices, organic rosemary extract, and potassium citrate. In some embodiments, the blend of phytochemical extracts is sourced from a group of fruits, vegetables, herbs, and spices, comprising one or more concentrates of broccoli sprouts, camu camu, tomato, acai, turmeric, garlic, basil, oregano, cinnamon, elderberry, chokeberry, raspberry, spinach, kale, Brussels sprouts, extracts of green *arabica* coffee bean, green tea, onion, apple, acerola, Japanese pagoda tree (quercetin), blackcurrant, blueberry, bilberry or any combination thereof.

In one embodiment, the fatty acids include organic medium chain triglycerides (MCT) and a balanced blend of omega-6 and omega-3 fatty acids. In another embodiment, the fatty acids include organic sunflower lecithin, organic flax seed oil and organic high linoleic sunflower oil. In one embodiment, the organic ingredient is a non-allergenic ingredient. In another embodiment, the organic ingredient comprises *vanilla* plant extract.

In one embodiment, the prebiotic fibers include organic inulin (from agave). In another embodiment, the nutritional composition further optionally comprises one or more vitamin and mineral blends, and purified water.

In exemplary embodiments, the vitamin and mineral blend is selected from a group of dicalcium phosphate, magnesium chloride, calcium carbonate, choline bitartrate, sodium ascorbate, trisodium citrate, potassium citrate, L-cysteine, Taurine, L-carnitine, inositol, L-tryptophan, DL-alpha-tocopheryl acetate, niacinamide, zinc oxide, ferric orthophosphate, calcium pantothenate, pyridoxine hydrochloride, copper sulfate, magnesium sulfate, riboflavin, thiamine hydrochloride, vitamin A palmitate, beta carotene, folic acid, biotin, chromium picolinate, phytonadione, sodium molybdate, sodium selenite, potassium iodide, vitamin D2 and vitamin B12.

In some embodiments, the nutritional composition further optionally comprises organic brown rice syrup solids, organic agave syrup, organic *quinoa* flour, organic *vanilla* flavor and organic milled chia.

In one embodiment, a method for producing the composition is disclosed. At one step, a protein slurry is formed by adding and mixing pea protein to water for ten minutes. At another step, a protein-fat slurry is formed by mixing fat to the protein slurry for five minutes. At another step, all dry ingredients are added to the protein-fat slurry and mixed for approximately five minutes. At another step, agave syrup is added to the mixture and mixed for approximately ten minutes. At another step, the composition is aseptically produced through a microthermics processor. These steps may be performed at ambient temperature and pressure.

Other objects, features and advantages of the present invention will become apparent from the following detailed description. It should be understood, however, that the detailed description and the specific examples, while indicating specific embodiments of the invention, are given by way of illustration only, since various changes and modifications within the spirit and scope of the invention will become apparent to those skilled in the art from this detailed description.

BRIEF DESCRIPTION OF DRAWINGS

The embodiments herein will be better understood from the following detailed description with reference to the drawings, in which:

FIG. 1 is a flowchart illustrating a method preparing the nutritional composition in an embodiment of the present invention.

DETAILED DESCRIPTION OF EMBODIMENTS

The described embodiments are to be considered in all respects only as illustrative and not restrictive. The scope of the invention is, therefore, indicated by the appended claims rather than by the foregoing description. All changes that come within the meaning and range of equivalency of the claims are to be embraced within their scope.

Embodiments of the invention are discussed below with reference to the examples. However, those skilled in the art will readily appreciate that the detailed description given herein with respect to these examples is for explanatory purposes as the invention extends beyond these limited embodiments. For example, it should be appreciated that those skilled in the art will, in light of the teachings of the present invention, recognize a multiplicity of alternate and suitable approaches, depending upon the needs of the particular application, to implement the functionality of any given detail described herein, beyond the particular implementation choices in the following embodiments described and shown. That is, there are numerous modifications and variations of the invention that are too numerous to be listed but that all fit within the scope of the invention. Also, singular words should be read as plural and vice versa and masculine as feminine and vice versa, where appropriate, and alternative embodiments do not necessarily imply that the two are mutually exclusive.

It is to be further understood that the present invention is not limited to the particular methodology, compounds, materials, manufacturing techniques, uses, and applications, described herein, as these may vary. It is also to be understood that the terminology used herein is used for the purpose of describing particular embodiments only and is not intended to limit the scope of the present invention. It must be noted that as used herein and in the appended claims, the singular forms “a,” “an,” and “the” include the plural reference unless the context clearly dictates otherwise. Thus, for example, a reference to “an element” is a reference to one or more elements and includes equivalents thereof known to those skilled in the art. Similarly, for another example, a reference to “a step” or “a means” is a reference to one or more steps or means and may include sub-steps and subservient means. All conjunctions used are to be understood in the most inclusive sense possible. Thus, the word “or” should be understood as having the definition of a logical “or” rather than that of a logical “exclusive or” unless the context clearly necessitates otherwise. Structures described herein are to be understood also to refer to functional equivalents of such structures. Language that may be construed to express approximation should be so understood unless the context clearly dictates otherwise.

Unless defined otherwise, all technical and scientific terms used herein have the same meanings as commonly understood by one of ordinary skill in the art to which this invention belongs. Preferred methods, techniques, devices, and materials are described, although any methods, techniques, devices, or materials similar or equivalent to those described herein may be used in the practice or testing of the present invention.

The present invention discloses a nutritional composition and method of using said nutritional composition. According to the present invention, the nutritional composition is a non-allergic nutritional composition, which constitutes organic and plant-based ingredients. In one embodiment, the nutritional composition comprises at least one of a protein source, one or more phytochemical extracts, one or more fatty acids, one or more non-allergic organic ingredients, and one or more prebiotic fibers. The organic ingredients are free of corn. The nutritional composition further comprises one or more vitamin and mineral blends, purified water and sea salt. In another embodiment, the nutritional composition further optionally comprises organic brown rice syrup solids, organic agave syrup, organic *quinoa* flour, organic *vanilla* flavor and organic milled chia. The nutritional composition is provided in liquid form for enteral and/or oral feeding. The present invention also provides an organic plant-based protein, which is a formulation of a vegan product free from the top eight allergens and corn.

In one embodiment, the protein source is an organic intact pea protein. The concentration of organic pea protein ranges from 5.50 wt % to 6.20 wt %. In one embodiment, the organic pea protein constitutes 6.13 wt % of the total composition and is approximately 100(%) of the total amount of protein in composition. In one embodiment, the organic pea protein is an organic intact pea protein.

In one embodiment, the pea protein is very easily digestible by humans as it has a protein digestibility-corrected amino acid score (PDCAAS) of 98% for the formulation and consequently delivers a full amino acid profile to the patient or user and services the needs of patients with impaired gastrointestinal absorption and digestion. In addition, branched-chain amino acids in the composition are essential nutrients, where normally the body obtains this type of amino acid from food, especially meat, dairy products, and legumes. In some embodiments, the branched-chain amino acids include leucine, isoleucine, and valine:

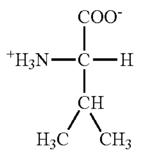

Valine

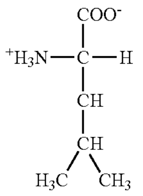

Leucine

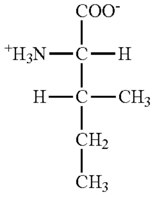

Isoleucine

Branched-chain amino acids stimulate the building of protein in muscle and possibly reduce muscle breakdown. Branched-chain amino acids prevent faulty message transmission in brain cells with advanced liver disease, mania, tardive dyskinesia, and other types of disease. Some pediatric nutritionists believe children would benefit from higher levels of BCAA's (branched-chain amino acids) than currently recommended. Pea protein is a rich source of BCAA's.

In one embodiment, the phytochemical extract is a blend of at least twenty-nine fruits, vegetables, herbs and spices. This natural supplement effects biological changes of oxidative and nitrosative stress markers (free radicals), nitric oxide levels, and cellular metabolic activity. In another embodiment, the phytochemical extracts include organic rosemary extract, blends of phytochemical extracts from fruits, vegetables, herbs, and spices, potassium citrate, magnesium citrate and potassium chloride. In some embodiments, the blends of phytochemical extracts from fruits, vegetables, herbs, and spices comprise any one or more of, concentrates of broccoli sprouts, camu camu, tomato, acai, turmeric, garlic, basil, oregano, cinnamon, elderberry, chokeberry, raspberry, spinach, kale, brussels sprouts, extracts of green *arabica* coffee bean, green tea, onion, apple, acerola, Japanese pagod tree (quercetin), blackcurrant, blueberry, bilberry or any combination thereof. The chemical structure of selected phytochemicals, such as, glucosinolate, sulforaphane, curcumin, genistein, phenoxodiol (synthetic genistein analog), epigallocatechin gallate (ECGC), lycopene and resveratrol are shown in Table 1.

TABLE 1

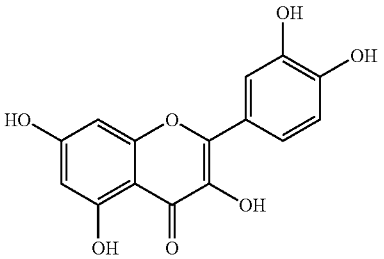

QUERCETIN

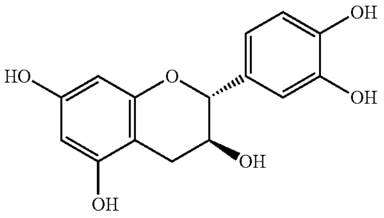

CATECHIN

TABLE 1-continued
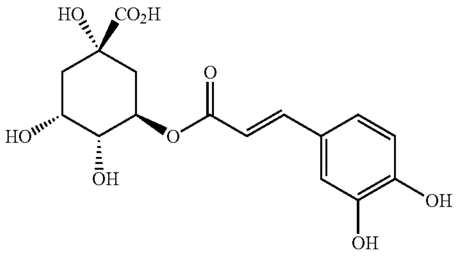
CHLOROGENIC ACID
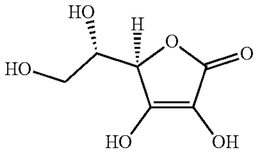
VITAMIN C
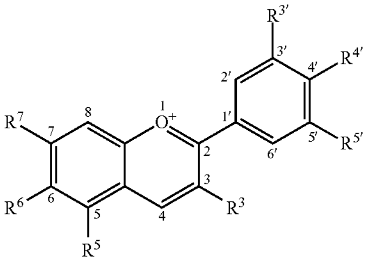
ANTHOCYANIN
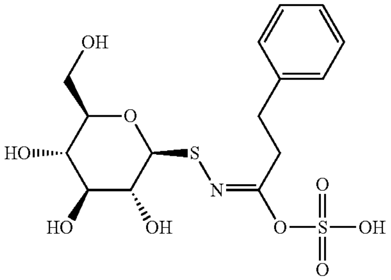
GLUCOSINOLATES
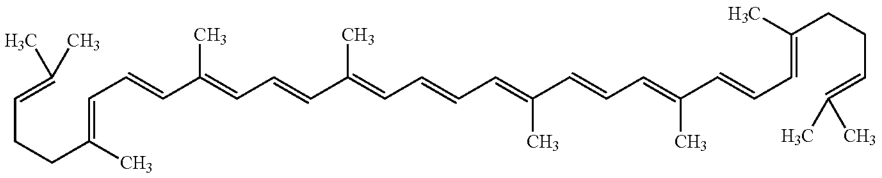
LYCOPENE
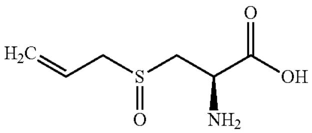
ALLIIN TABLE 1-continued

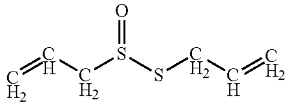

ALLICIN

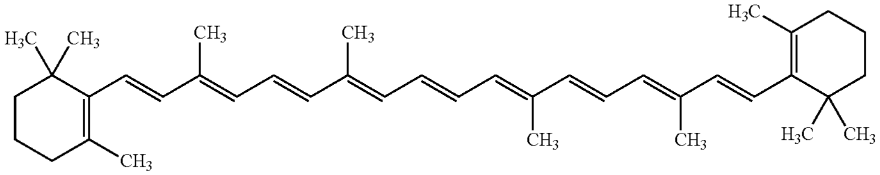

BETA CAROTENE

In one embodiment, the maximum concentration of organic rosemary extract is 0.05 wt %. In another embodiment, the minimum concentration of organic rosemary extract is 0.01 wt %. In one embodiment, the organic rosemary extract constitutes 0.03 wt % of the total composition. The rosemary-based extract is a natural oxidation-inhibiting product. In one embodiment, the maximum concentration of a blend of phytochemical extracts from fruits, vegetables, herbs, and spices is 0.03 wt %. In another embodiment, the minimum concentration of a blend of phytochemical extracts from fruits, vegetables, herbs, and spices is 0.01 wt %. In one embodiment, a blend of phytochemical extracts from fruits, vegetables, herbs, and spices constitutes 0.05 wt % of the total composition. The blend of phytochemical extracts is sourced from twenty-nine fruits, vegetables, herbs, and spices.

In one embodiment, the potassium citrate constitutes 0.11 wt %, which is obtained from potassium source. In one embodiment, the magnesium citrate constitutes 0.01 wt %, which is obtained from magnesium source.

In one embodiment, the fatty acids contain a balanced blend of essential omega-6 fatty acids, such as sunflower and flax, and omega-3 fatty acids, such as ALA (alpha-linolenic acid) from flax, and easily digestible medium chain triglycerides (MCT) from coconut oil. In one embodiment, the omega-6 fatty acid is an essential fatty acid. Omega-3 has many anti-inflammatory properties, and MCT is easily digestible, which acts as an immediate energy source via portal vein. In one embodiment, the MCT and long chain triglycerides (LCT) ratio is optimized to 40:60, and the Omega 6 and Omega 3 ratio is formulated to 4:1. In one embodiment, the maximum concentration of organic medium chain triglycerides is 1.80 wt %. In another embodiment, the minimum concentration of organic medium chain triglycerides is 1.00 wt %. In one embodiment, the concentration of organic medium chain triglycerides is 1.12 wt %. In some embodiments, the MCT is a form of saturated fatty acids from coconut with medium-chain fats between 6-12 carbons.

In one embodiment, the composition comprises organic sunflower lecithin, organic flax seed oil, and organic high linoleic sunflower oil. In some embodiments, the concentration of organic sunflower lecithin is 0.01 wt %, and in others it is between 0.05 and 0.1. Lecithin is a naturally occurring substance found in the membranes of living cells. Lecithin is extracted from sunflower seeds.

In one embodiment, the maximum concentration of organic flax seed oil is 0.80 wt %. In another embodiment, the minimum concentration of organic flax seed oil is 0.48 wt %. In one embodiment, the concentration of organic flax seed oil is 0.77 wt %. The organic flax seed oil is a colorless to yellowish oil obtained from the dried, ripened seeds of the flax plant.

In one embodiment, the maximum concentration of organic high linoleic sunflower oil is 1.75 wt %. In another embodiment, the minimum concentration of organic high linoleic sunflower oil is 1.50 wt %. In one embodiment, the concentration of organic high linoleic sunflower oil is 1.55 wt %. The organic high linoleic sunflower oil is a variety of sunflower oil containing nearly 70% polyunsaturated linoleic acid.

In one embodiment, the organic ingredients are non-allergenic ingredients. In another embodiment, the organic ingredients include *vanilla* plant extract. The *vanilla* plant extract contains several medicinal properties, which could be useful for tackling several ailments. It is also a rich constituent of flavonoids, alkaloids, glycosides, carbohydrates and several other phytochemicals. The *vanilla* plant extract also contains both analgesic, antispasmodic, antioxidant and anti-inflammatory properties.

In one embodiment, the vitamin and mineral blend is selected from a group of vitamins and minerals comprised of: dicalcium phosphate, magnesium chloride, calcium carbonate, choline bitartrate, sodium ascorbate, trisodium citrate, potassium citrate, L-cysteine, taurine, L-carnitine, inositol, L-tryptophan, DL-alpha-tocopheryl acetate, niacinamide, zinc oxide, ferric orthophosphate, calcium pantothenate, pyridoxine hydrochloride, copper sulfate, magnesium sulfate, riboflavin, thiamine hydrochloride, vitamin A palmitate, beta carotene, folic acid, biotin, chromium picolinate, phytonadione, sodium molybdate, sodium selenite, potassium iodide, vitamin D2 and vitamin B12.

In one embodiment, the maximum concentration of vitamin and mineral blend is 0.95 wt %. In another embodiment, the minimum concentration of vitamin and mineral blend is 0.80 wt %. In one embodiment, the concentration of vitamin and mineral blend is 0.92 wt %. The vitamin and mineral blend is a blend of vitamins, minerals and amino acids.

In one embodiment, the maximum concentration of purified water is 78.00 wt %. In another embodiment, the minimum concentration of purified water is 73.00 wt %. In one embodiment, the concentration of purified water is 76.49 wt %, which is obtained from a water source.

In one embodiment, the prebiotic fibers include organic inulin (from agave). In one embodiment, the maximum concentration of organic inulin is 1.14 wt %. In another embodiment, the minimum concentration of organic inulin is 0.95 wt %. In one embodiment, the concentration of organic inulin is 1.00 wt %. The organic agave inulin is a highly soluble dietary fiber (inulin-type fructan) that provides numerous health benefits. Inulin serves as a "fertilizer" to sustain beneficial bifidobacteria in the large intestine.

The prebiotic fiber is clinically proven to be easy to digest (due to low gas potential) and promote the growth of good bacteria in the gut such as bifidobacteria. Further, fecal actinobacteria and *Bifidobacterium* were enriched 3- and 4-fold after ingestion of agave inulin, a long chain fructo-oligosaccharide (FOS), and *desulfovibrio* were depleted 40% with agave inulin. Agave inulin tended to reduce fecal 4-methylphenol and pH. A positive association between intakes of agave inulin and *Bifidobacterium* is briefly described herein. Total dietary fiber from agave inulin was positively associated with fecal butyrate and tended to be positively associated with *bifidobacterium* and was negatively correlated with *desulfovibrio* abundance. A long-chain FOS could foster *Bifidobacterium* colony growth, which could also serve as food for less desirable strains of bacteria. A use of a short-chain FOS such as Chicory inulin encourages the growth of *Klebsiella*, a bacterium at work in ankylosing spondylitis, which causes problems with intestinal permeability and is therefore not optimal for digestion. It also feeds *E. coli* and many *Clostridium* species, which are inharmonious with gut-friendly bacteria.

In one embodiment, the nutritional composition further optionally comprises organic brown rice syrup solids and organic agave syrup. In one embodiment, the maximum concentration of organic brown rice syrup solid is 10.00 wt %. In another embodiment, the minimum concentration of organic brown rice syrup solid is 4.00 wt %. In one embodiment, the concentration of organic brown rice syrup solid is 4.58 wt %.

In one embodiment, the maximum concentration of organic agave syrup is 7.00 wt %. In another embodiment, the minimum concentration of organic agave syrup is 2.85 wt %. In yet another embodiment, the concentration of organic agave syrup is 6.00 wt %. The organic agave syrup is a natural alternative to refined sugars and artificial sweeteners, extracted from the agave plant. Agave syrup is fructose which is a slowly digested carbohydrate which does not spike blood sugar upon ingestion.

In one embodiment, the nutritional composition further optionally comprises organic *quinoa* flour in the concentration of 0.03 wt %. The organic *quinoa* flour is a ground powder from the seeds of *Salvia hispanica*, commonly known as chia, a species of flowering plant in the mint family, lamiaceae, native to central and southern Mexico and Guatemala. In another embodiment, the nutritional composition further optionally comprises organic *vanilla* flavor in the concentration of 1.10 wt %, which is derived from orchid seed pods of the genus *Vanilla*. In another embodiment, the nutritional composition further optionally comprises organic milled chia in the concentration of 0.01 wt %.

In one embodiment, the nutritional composition further optionally comprises dipotassium phosphate and organic Dutch cocoa powder. The dipotassium phosphate serves as a source of phosphorus and potassium. In one embodiment, the maximum concentration of dipotassium phosphate is 0.14 wt %. In another embodiment, the minimum concentration of dipotassium phosphate is 0.13 wt %. In one embodiment, the concentration of dipotassium phosphate is 0.14 wt %.

In another embodiment, the organic Dutch cocoa powder are the solids which remain after cocoa butter is extracted from cacao beans. In one embodiment, the maximum concentration of organic Dutch cocoa powder is 1.50 wt %. In another embodiment, the minimum concentration of organic Dutch cocoa powder is 1.00 wt %. In one embodiment, the concentration of organic Dutch cocoa powder is 1.25 wt %.

In one embodiment, the nutritional composition further optionally comprises organic gum acacia Senegal. Gum acacia Senegal is a complex polysaccharide indigestible to both humans and animals and considered a safe dietary fiber combined with gellan gum, a water-soluble anionic polysaccharide produced by the bacterium *Sphingomonas elodea*. In one embodiment, the maximum concentration of organic gum acacia Senegal is 2.00 wt %. In another embodiment, the minimum concentration of organic gum acacia Senegal is 0.13 wt %. In one embodiment, the concentration of organic gum acacia Senegal is 0.15 wt %.

In one embodiment, the nutritional composition further optionally comprises tricalcium phosphate. Tricalcium phosphate provides a source of calcium and phosphorus. In one embodiment, the maximum concentration of tricalcium phosphate is 0.05 wt %. In another embodiment, the minimum concentration of tricalcium phosphate is 0.02 wt %. In one embodiment, the concentration of tricalcium phosphate is 0.03 wt %.

The composition should contain a therapeutically effective amount of each ingredients, and also those described in Table 2. The ingredients of the therapeutic composition according to the present invention are summarized in Table 2 below with respect to a description thereof, the active ingredients therein, percentages by weight range for each active ingredient, and the benefits thereof.

TABLE 2

| Ingredient | Minimum Range % | Current % | Maximum Range % | Description |
|---|---|---|---|---|
| Dipotassium phosphate | 0.13 | 0.14 | 0.14 | Source of phosphorus and potassium |
| Organic agave syrup | 2.85 | 6.00 | 7.00 | A natural alternative to refined sugars and artificial sweeteners from the agave plant |
| Organic brown rice syrup solids(20de) | 4.00 | 4.58 | 10.00 | An alternative to refined sugar that sweetens without increasing blood sugar levels. |
| Organic Dutch cocoa powder | 1.00 | 1.25 | 1.50 | The solids remaining after cocoa butter is extracted from cacao beans |

TABLE 2-continued

| Ingredient | Minimum Range % | Current % | Maximum Range % | Description |
|---|---|---|---|---|
| Organic flax seed oil | 0.48 | 0.77 | 0.80 | A colorless to yellowish oil obtained from the dried, ripened seeds of the flax plant |
| Organic gum acacia, organic gellan gum | 0.13 | 0.15 | 2.00 | Gum *Acacia Senegal* is a complex polysaccharide indigestible to both humans and animals and considered a safe dietary fiber combined with Gellan gum, a water-soluble anionic polysaccharide produced by the bacterium *Sphingomonas elodea.* |
| Organic high linoleic sunflower oil | 1.50 | 1.55 | 1.75 | Variety of sunflower oil containing nearly 70 percent polyunsaturated linoleic acid |
| Organic inulin | 0.95 | 1.00 | 1.14 | Agave inulin is a highly soluble dietary fiber (inulin-type fructan) that has been shown by scientific studies to provide numerous health benefits. Inulin serves as a "fertilizer" to sustain beneficial Bifidobacteria in the large intestine. |
| Organic medium chain triglycerides (derived from coconut) | 1.00 | 1.12 | 1.80 | A form of saturated fatty acid from coconut with medium-chain fats that have between 6-12 carbons |
| Organic milled chia | 0.01 | 0.01 | 0.01 | A ground powder from the seeds of *Salvia hispanica*, commonly known as chia, is a species of flowering plant in the mint family, Lamiaceae, native to central and southern Mexico and Guatemala. |
| Organic pea protein | 5.50 | 6.13 | 6.20 | Pea protein isolate is extracted commonly from the yellow garden pea (*Pisum sativum*), which contain fleshy greenish seeds |
| Organic quinoa flour | 0.03 | 0.03 | 0.03 | Ground Quinoa seeds from a flowering plant in the amaranth family |
| Organic rosemary extract | 0.03 | 0.03 | 0.03 | Rosemary-based extract is a natural oxidation-inhibiting product |
| Organic superfoods blend | 0.03 | 0.03 | 0.03 | The Spectra ™ Superfoods Blend is a blend of phytochemical extracts from 29 fruits and vegetables. |
| Organic sunflower lecithin | 0.10 | 0.10 | 0.10 | Lecithin is a naturally occurring substance found in the membranes of living cells. Lecithin is extracted from sunflower seeds. |
| Organic vanilla flavor | 1.10 | 1.10 | 1.10 | Flavor derived from orchid seed pods of the genus *Vanilla* |
| Potassium citrate | 0.11 | 0.11 | 0.11 | Source of potassium |
| Purified water | 73.00 | 76.49 | 78.00 | Source of water |
| Tricalcium phosphate | 0.02 | 0.03 | 0.05 | Source of calcium and phosphorus |
| Vitamin and mineral blend | 0.80 | 0.92 | 0.95 | Source of 25 vitamins, minerals and amino acids |

In an embodiment, the therapeutic effects of the nutrition composition are numerous. The nutrition composition comprises agave syrup. It contains a higher level of fructose than high fructose corn syrup. An important difference is that fructose is up to twice as sweet as sucrose, and sweeter than high fructose corn syrup. Unlike table sugar or HFCS, fructose does not cause a rapid rise and subsequent large fall in blood glucose levels, which means it has a low glycemic load or glycemic index (GI). The glycemic index is a value assigned to foods based on how slowly or how quickly those foods cause increases in blood glucose levels. The blood glucose levels above normal are toxic and can cause blindness, kidney failure, or increase cardiovascular risk. Food components that are low on the glycemic index (GI) scale tend to release glucose slowly and steadily. Food components that are high on the glycemic index release glucose rapidly. Low GI foods tend to foster weight loss, while foods high on the GI scale help with energy recovery after exercise, or to offset hypo- (or insufficient) glycemia. For an average diet, there are no health problems associated with fructose except for some individuals, who may be fructose intolerant.

Fructose was given GRAS status in 1983 and was reconfirmed in 1996 after a study of the available clinical trials on the effects of fructose consumption. Fructose has a low glycemic index, which can be used to help control blood glucose levels in concern with a total diet plan. Agave syrup is not processed in the same manner as corn syrup. Agave naturally contains inulin, a long chain fructose molecule. Fructose, sometimes known as fruit sugar, exists naturally in fruits and honey as a single unit of fructose. It exists naturally in inulin as a long chain of fructose molecules linked together, similar to the glucose chains in starch. The bonds in inulin can be broken to make free fructose. When a person eats a food containing inulin, the body's enzymes do not break down the inulin. Instead, the inulin is consumed by bacteria in the intestine. The bacteria that consume the inulin tend to be the beneficial bacteria, the same types found in yogurts and various probiotic foods. As the inulin feeds these beneficial organisms, allowing them to outcompete the detrimental intestinal organisms, inulin is labeled a prebiotic and has many health benefits. While fructose could be made by hydrolyzing or breaking the bonds of inulin, it could also be made by using an isomerase enzyme to change glucose into fructose.

In one embodiment, the composition comprising the organic brown rice syrup solid (BRSS) is a natural alternative to refined sugars and artificial sweeteners from the agave plant. Unlike refined table sugar, which causes the body to work harder to absorb the sucrose, brown rice syrup is able to provide the body with fiber, as well as 3% of a user's recommended daily intake of sodium and potassium. As the rice syrup solids are boiled and the liquid is removed, the result is a complex of simple sugars. This facilitates slower absorption of the sugars in rice syrup by the digestive system. This is a huge advantage because in the case of regular table sugar, there is rapid swell in blood sugar level with buildup of excess fat with time. The slower absorption of the sugars also allows the user or patient to maintain their energy and prevents the negative effects of sugar including fatigue, irritability and the desire for more sugar.

All these properties indicate that BRSS also have a low glycemic index. The use of the natural sweetening ability of BRSS is unique in the space of medical grade sole source nutrition. BRSS are a far superior option than maltodextrin, commonly used as a carbohydrate in comparable products. Maltodextrin is used as a thickener, filler or preservative in many processed foods. It is an artificially produced white powder that can be enzymatically derived from any starch but is commonly made from corn, rice, potato starch or wheat. Maltodextrin is also used in carbohydrate supplements that are marketed to athletes and bodybuilders as a way to boost their energy levels. However, consuming maltodextrin leads to spiked blood sugar, suppresses the growth of probiotics, toxically affects several bodily organs and systems, and causes allergic reactions or side effects because it is derived from corn.

In one embodiment, the organic flax seed oil is derived from the extremely nutritious and disease-preventing flax seed. The flax seed oil has a high concentration of healthy omega-3s as fatty acids associated with healthier brains and hearts, better moods, decreased inflammation, and healthier skin and hair. Flax seed oil contains 50% to 60% of omega-3 fatty acids in the form of alpha-linolenic acid (ALA). Flax seed is the richest plant source of the omega(ω)-3 fatty acid, i.e. α-linolenic acid (ALA). Flax seed oil is low in saturated fatty acids (9%), moderate in monosaturated fatty acids (18%), and rich in polyunsaturated fatty acid (73%). Of all lipids in flaxseed oil, α-linolenic acid is the major fatty acid ranging from 39% to 60.42% followed by oleic, linoleic, palmitic and stearic acids, and provides an excellent omega (ω)-6:omega(ω)-3 fatty acid ratio of approximately 0.3:1. Flax seed oil is naturally high in anti-oxidants like tocopherols and beta-carotene. Flax seed oil provides basic nutrition as well as various health benefits in reducing cancer and cardiovascular diseases, lowering LDL-cholesterol and vasodilatory functions. Therefore, flax seed oil could be considered as a functional food. Flax seed oil is emerging as an important functional food ingredient, because of its rich contents of α-linolenic acid (ALA, omega-3 fatty acid), lignans, and fiber. Flax seed oil, fibers and flax lignans have potential health benefits such as, in reduction of cardiovascular disease, atherosclerosis, diabetes, cancer, arthritis, osteoporosis, autoimmune and neurological disorders.

The organic high linoleic sunflower oil comprises essential omega-6, impressive fatty acid content, which includes palmitic acid, stearic acid, oleic acid, and linoleic acid. The combination of fatty acids in the body are extremely important to maintain various elements of human health, and sunflower oil could help to maintain the balance. The balance of fatty acids found in sunflower oil, including a substantial amount of linoleic acid (an omega-6 fatty acid) is optimal for patients. Finding a healthy balance between HDL or good cholesterol (omega-3s) and LDL or bad cholesterol is very important to the health of patients. Furthermore, sunflower oil does not contain any saturated fats, which means that it could actually reduce overall cholesterol content in the body. Omega-6 (n−6) polyunsaturated fatty acids (PUFA) in High Linoleic Sunflower Oil (e.g., arachidonic acid (AA)) and omega-3 (n−3) PUFA (e.g., eicosapentaenoic acid (EPA)) are precursors to potent lipid mediator signaling molecules, termed "eicosanoids," which have important roles in the regulation of inflammation.

The composition in embodiments is engineered to have an optimal combination of omega-3 and omega-6 fatty acids which are types of essential fatty acids that are not generated on our own, and have to be obtained from diet. Both are polyunsaturated fatty acids that differ from each other in their chemical structure. There are two critical omega-3 fatty acids, (EPA and DHA), that patients require. Furthermore, vegetarian sources, which the present composition utilizes, such as chia seeds and flax seeds contain a precursor omega-3 (alpha-linolenic acid called ALA) that the body must convert to EPA and DHA. EPA and DHA are the building blocks for hormones that control immune function, blood clotting, and cell growth as well as components of cell membranes.

In contrast, omega-6 foods containing these fatty acids are numerous in modern diets. They are found in seeds and nuts, and the oils are extracted from them. The body also constructs hormones from omega 6 fatty acids. In general, hormones derived from the two classes of essential fatty acids have opposite effects. Those from omega-6 fatty acids tend to increase inflammation (an important component of the immune response), blood clotting, and cell proliferation, while those from omega-3 fatty acids decrease those functions. Both families of hormones must be in balance to maintain optimum health, so there are some omega-6 benefits. Many nutrition experts believe that before we relied so heavily on processed foods, humans consumed omega-3 and omega-6 fatty acids in roughly equal amounts. The imbalance between omega-3 and omega-6 fatty acids may also contribute to obesity, depression, dyslexia, hyperactivity and even a tendency toward violence. Bringing the fats into proper proportion may actually relieve those conditions. The composition of the present invention has a unique 3:1 and 4:1 ratio of omega 6:omega 3 ratio, which facilitates balance of these fatty acids and contributes to the anti-inflammatory effects of them. In optional embodiments, the MCT:LCT ratio is optimized to 4:6 while the Omega 6:Omega 3 ratio is formulated to 4:1.

The nutrition composition further comprises agave inulin, which is a highly soluble dietary fiber (inulin-type fructan) that provides numerous health benefits. Inulin serves as a "fertilizer" to sustain beneficial bifidobacteria in the large intestine. Inulin is clinically proven to be easy to digest and promotes the growth of good bacteria in the gut such as bifidobacteria. In studies, fecal actinobacteria and *bifidobacterium* were enriched 3- and 4-fold after ingestion of agave inulin, a long chain fructo-oligosaccharide (FOS), and *desulfovibrio* was depleted 40% with agave inulin compared with the control. Agave inulin tended to reduce fecal 4-methylphenol and pH. Total dietary fiber from agave inulin has been positively associated with fecal butyrate and tended to be positively associated with *Bifidobacterium* and was negatively correlated with *desulfovibrio* abundance. Organic inulin could be used in everyday life as a prebiotic and food supplement that stimulates the growth and activity of good bacteria in the body.

The nutrition composition further comprises medium-chain triglycerides (MCT) oil which is quickly and easily digested and provides a relatively large amount of energy to the patient. They (MCT) are associated to stimulate the metabolism and have been identified as a potential weight loss aid. If MCT oil is consumed to increase weight gain, a substantial amount of protein would aid in weight gain. Medium-chain triglycerides are easily absorbed by the gastrointestinal tract and converted into energy by the liver. They are often digested well even by those who cannot digest normal, long-chain fatty acids. MCT are comprised of primarily caprylic and capric fatty acids. MCT help to treat diseases such as cystic fibrosis, and fat malabsorption. They have also been used to add calories to infant and certain other formulas. Unlike other fats, MCT oil benefits because it does not go through the lymphatic system, and instead is transported directly to the liver where it is metabolized so it releases energy like a carbohydrate and creates ketones.

The nutrition composition comprising organic milled chia is a good source of omega-3 fatty acids, which could be used as whole or ground. The organic milled chia is good for intestinal function. There are two critical omega-3 fatty acids, (EPA and DHA), that the body needs. Vegetarian sources, such as chia seeds and flax seeds contain a precursor omega-3 (alpha-linolenic acid called ALA) that the body must convert to EPA and DHA. EPA and DHA are the building blocks for hormones that control immune function, blood clotting, and cell growth as well as components of cell membranes. Chia seeds act as functional foods and may contribute to a better adherence to the dietary treatment in controlling hypercholesterolemia. Chia seeds have an impact on the concentration of total cholesterol (C), LDL-C, HDL-C and lipoprotein. Significant decrease in serum LDL cholesterol was accompanied by a decrease in the concentration of small LDL particles. In addition, systolic and diastolic blood pressure decreases significantly as well as total body weight and BMI.

The nutrition composition further comprises organic *quinoa* flour, which itself comprises higher dietary fiber content than in other grains. This fiber helps improve intestinal functions. In addition, two flavonoids that have been particularly well studied are quercetin and kaempferol, which are found in large amounts in *quinoa*. In fact, the quercetin content of *quinoa* is even higher than typical high-quercetin foods like cranberries. These molecules have anti-inflammatory, anti-viral, anti-cancer and anti-depressant effects. Quercetin, a polyphenolic compound and a major bioflavonoid in the human diet, has anti-inflammatory properties and enhances energy expenditure. Naturally occurring flavonoids inhibit three reverse transcriptases. *Quinoa* is also gluten-free, making it an optimal choice for patients with celiac or gluten intolerances. Using *quinoa* instead of typical gluten-free ingredients like refined tapioca, potato, corn and rice flour, dramatically increases the nutrient and antioxidant value of the diet. Henceforth, the composition according to the present invention is gluten-free.

The nutrition composition further comprises organic rosemary extract which has been shown to boost memory, improve mood, reduce inflammation, relieve pain, protect the immune system, stimulate circulation, detoxify the body, protect the body from bacterial infections, prevent premature aging, heal skin conditions, and alleviate digestion problems, including heartburn, intestinal gas (flatulence), liver and gallbladder complaints and loss of appetite. The chemical in rosemary primarily responsible for antioxidation properties is carnosol, a phenolic diterpene also found in mountain desert sage. In addition to being a rich antioxidant, carnosol is also known for its anti-cancer and anti-inflammatory properties. According to a recent article published in the journal Cancer Letters, "Carnosol has been evaluated for anticancer property in prostate, breast, skin, leukemia, and colon cancer with promising results". It has also been discovered that carnosol targets cells to reduce inflammation and can also balance androgen and estrogen in the body, reduce cancer risks, increase nerve growth factor healing nerve tissue, and may have a selective toxicity towards cancer cells versus nontumorigenic cells.

The nutrition composition comprising organic sunflower lecithin is good for heart health. It helps to prevent and reverse damage from coronary disease. Lecithin is essentially an emulsifier of fat which could be used by the body to discard excess fat from the bloodstream. These excess fats include cholesterol and triglycerides, therefore it will help reduce and control levels of cholesterol. A high concentration of linoleic acid present in sunflower lecithin helps to perform the above process. In addition, olive oil has similar levels of linoleic acid. Phospholipids also play a vital essential role for liver health and prevent excessive accumulation of fat.

Further, another advantage of using sunflower lecithin is the extraction process. Sunflower lecithin gets extracted without the need for potentially damaging chemical solvents such as acetone and hexane. Sunflower lecithin is produced through a cold press system, a system also used to derive oil from olives and similar products. Sunflower lecithin is abundant with essential choline and fatty acids, such as phosphatidylinositol.

The nutrition composition comprising organic *vanilla* flavor soothes inflammation throughout the body. This is particularly effective for inflammation of the liver, which occurs due to numerous reasons, especially for immunocompromised individuals. Vanillin could help ease arthritis, gout and other inflammatory conditions. *Vanilla* extract has been evaluated for hepatoprotective activity against paracetamol-induced liver damage in rats. The researchers orally administered an ethanolic extract of *Vanilla planifolia* or a control reference solution to experimental animals with hepatotoxicity induced by paracetamol. It was observed that the plant extract was able to protect the liver against the injury induced by paracetamol in rats. This was proven by the tremendous reduction in serum enzymes alanine aminotransferase (ALT), aspartate aminotransferase (AST), alkaline phosphatase (ALP) and bilirubin. The ethanolic extract of *Vanilla planifolia* has hepatoprotective activity against paracetamol-induced hepatotoxicity in rats. *Vanilla* extract components were studied for the potential use as antioxidants for food preservation and as nutraceuticals in health supplements. The extract and pure standard compounds were screened to ascertain their antioxidant properties using β-carotene-linoleate and diphenyl picryl hydrazyl (DPPH) in vitro model systems. Interestingly, the study observed and supported the potential use of *vanilla* bean extracts as antioxidants.

The nutrition composition further comprises potassium citrate, which is an essential nutrient for homeostasis in the body. It works alongside sodium to maintain normal blood pressure. Potassium is known as an electrolyte, helps to maintain a healthy fluid balance in the body. It also helps to transmit electrical pulses to allow proper nerve and muscle function. Potassium citrate is specifically used to help maintain effective body pH.

The nutrition composition further comprises a blend of phytochemical extracts from fruits, vegetables, herbs, and spices, which have been reported to decrease reactive oxygen species (ROS), increase cellular oxygen consumption in blood and mitochondria, decrease extracellular $H_2O_2$, and reduce TNFα-induced inflammatory response in humans. Phytochemicals are the active ingredients that promote whole body health. The extracts do not contain any source ingredients such as protein, fat, or carbohydrates. The blend may include extracts of green tea and green coffee but does not contain any caffeine. A blend of phytochemical extracts from fruits, vegetables, herbs, and spices represents the latest evolution in the fight against potentially-damaging free radicals. The biological effects of a natural supplement on the changes of oxidative and nitrosative stress markers, as well as cellular metabolic activity, have been clinically observed in the human body. The blend of phytochemical extracts has been reported to decrease ROS, increase cellular oxygen consumption in blood and mitochondria, decrease extracellular $H_2O_2$, and reduce TNFα-induced inflammatory response in humans. Administration of a blend of phytochemical extracts resulted in statistically significant long-term inhibition of mitochondrial and cellular ROS generation by as much as 17% as well as 3.5-times inhibition in extracellular NADPH system-dependent generation of $O_2$, and nearly complete inhibition of extracellular $H_2O_2$ formation. This was reflected in more than two times inhibition of ex vivo cellular inflammatory response and also increases in bioavailable NO concentration. Further, there was measured synergetic, biological effects of a natural supplement on changes in OSM and cellular metabolic activity. The unique design and activity of the plant-based natural supplement, in combination with the newly developed and extended Vitality test, demonstrates the potential of using dietary supplements to modulate OSM and also opens the door to future research into the use of natural supplements for supporting optimal health.

The nutritional component further comprises tricalcium phosphate, which is a calcium salt of phosphoric acid and acts as a source of calcium and phosphorus. Tricalcium phosphate consists of positively charged particles of calcium combined with negatively charged particles called phosphates, which have the chemical formula $PO_4$.

The nutritional component further comprises dipotassium phosphate, which is a highly water-soluble salt that acts as a source of phosphorus and potassium. Dipotassium phosphate commonly comes in the form of a colorless, white substance. Potassium is one of the seven essential macro minerals, of which your body requires at least 100 nmilligrams on a daily basis in order to sufficiently support its key processes. A healthy intake of potassium decreases your risk of stroke, lowers your blood pressure, protects you against the loss of muscle mass, preserves your bone mineral density, and reduces the risk of kidney stones.

The nutritional component further comprises organic Dutch cocoa powder, which is comprised of solids that remain after cocoa butter is extracted from cacao beans. Dutch process cocoa powder (also sometimes called "alkalized," "European style," or "Dutched") is washed with a potassium carbonate solution that neutralizes cocoa's acidity to a pH of 7. Although all cocoa powders can vary in color from light reddish brown to a richer dark brown, the Dutch process gives the powder a noticeably darker hue. This is different from natural cocoa powder, which is naturally acidic and typically has a pH between 5 and 6.

The nutritional component further comprises organic gum acacia/organic gellan gum, which is a complex polysaccharide indigestible to both humans and animals and considered a safe dietary fiber combined with Gellan gum, a water-soluble anionic polysaccharide produced by the bacterium *Sphingomonas elodea*. Acacia gum is a natural gum consisting of the hardened sap of various species of the acacia tree. It is a complex mixture of glycoproteins and polysaccharides, and is the original source of the sugars arabinose and ribose. Gellan gum is used as a thickener or stabilizer, and when used in very small doses it acts as an anti-settling agent in liquids. Gellan gum is created by the microbial fermentation of sugar, a natural process, and is vegetarian and Kosher approved.

According to the present invention, the biological biologically active compounds and total antioxidant capacity assay (TAC) of a blend of phytochemical extracts per serving size of 100 mg is shown in below Table 3.

TABLE 3

| Phytochemical compound | Units | Result |
|---|---|---|
| Glucosinolates | Mg | 0.1 |
| Quercetin | Mg | 10.8 |
| Lycopene | Mg | 43 |
| Chlorogenic acids | Mg | 6.7 |
| Vitamin C | Mg | 1.2 |
| Catechins | Mg | 10.3 |
| Allicin | Mg | 10 |
| Alliin | Mg | 20 |
| Anthocyanins | Mg | 0.5 |
| Vitamin E | Mg | 13.4 |
| Beta-carotene | Mg | 36.4 |
| Folate | Mg | 1.2 |
| Vitamin K | μg | 3.1 |
| Calcium | mg | 0.77 |

TABLE 3-continued

| Phytochemical compound | Units | Result |
| --- | --- | --- |
| Magnesium | mg | 0.53 |
| Potassium | mg | 4.3 |
| Activity against individual radicals | | |
| Activity against peroxyl radicals | μmol TE | 1070 |
| Activity against hydroxyl radicals | μmol TE | 1511 |
| Activity against peroxynitrite | μmol TE | 110 |
| Activity against superoxide anion | μmol TE | 1337 |
| Activity against singlet oxygen | μmol TE | 417 |
| Total activity | μmol TE | 4445 |

(Source: Phytochemical Composition and Antioxidant Capacity of Three Malian Medicinal Plant Parts François Muanda, 1 Donatien Koné, 1 Amadou Dicko, 1, *Rachid Soulimani, 2 and Chafique Younos https://www.ncbi.nlm.nih.gov/pmc/articles/PMC4256589)

The nutrition composition further comprises dipotassium phosphate, which is a source of phosphorous and potassium.

With reference now to Table 4, an amino acid profile of the composition is show shown as it relates to cow's milk.

TABLE 4

| Amino Acid Profile (Essential) | | | |
| --- | --- | --- | --- |
| | Composition | Cow's M | Variance (%) |
| Histidine | 5.16 | 5.03 | 103 |
| Branched Chain Amino Ac Total: | 44.8 | 45.36 | 95 |
| Leucine | 19.04 | 18.56 | 103 |
| Isoleucine | 11.56 | 12.11 | 96 |
| Lysine | 14.17 | 14.69 | 115 |
| Methionine | 7.25 | 6.31 | 102 |
| Phenylalanine | 19.14 | 18.81 | 102 |
| Threonine | 8.96 | 8.76 | 97 |
| Tryptophan | 2.64 | 2.71 | 93 |
| Valine | 12.08 | 13.02 | 93 |

It was found in a two-tailed t-test that there were no significant differences in the amino acid profiles of the two protein sources (p-value >0.99 NS). Hence, essential amino acid profiles are equivalent in protein quality.

Referring now to FIG. 1, a method 100 for preparing the nutritional composition is illustrated. In an embodiment, the method comprises forming a protein slurry by adding and mixing pea protein to water for ten minutes, at step 102. At step 14, a protein-fat slurry is formed by mixing fat to the protein slurry for five minutes. At step 106, all dry ingredients are added to the protein-fat slurry and mixed for five minutes. At step 108, agave syrup is added to the mixture and mixed for ten minutes. At step 110, the composition is aseptically produced through a microthermics processor.

The nutritional composition further needs to be heated to a prescribed temperature for a prescribed time period. The specific temperatures and times depend on the food involved. Ultra-high temperature (UHT) treatment takes place in optimized heat exchangers before packaging. This process minimizes heat penetration problems and allows very short heating and cooling times, at the same time minimizing unwanted changes in the taste and nutritional properties of the composition.

The aseptic package is sterilized prior to filling with UHT treated food, resulting in a product which is shelf stable for over 6 months. The Aseptic packaging method passes flat, unformed packaging material through a heated hydrogen peroxide bath. A hydrogen peroxide concentration of 30% is heated at 70° C. for six seconds. Hydrogen peroxide is then eliminated from the packaging material using pressure rollers or hot air.

The environment where food is handled and sealed is free of potentially contaminating bacteria. Further, the filling and sealing machinery are sterilized before packaging and during the production process. Sterilization can be done using hot air and steam or by combining heat treatment with hydrogen peroxide chemical sterilization.

Advantageously, the present invention is entirely plant-based and free of the top eight allergens such as milk, wheat, soybeans, eggs, peanuts, tree nuts, fish and shellfish, and corn, and is non-GMO (free of genetically modified organisms). In addition, it contains organic ingredients, optimal fatty acid ratios, oxidation fighting ingredients, anti-inflammatory properties and beneficial fiber. Alternative approaches to the problem include formation of a blended food product. The composition is made with 100% pea protein hydrolysates for optimal digestion.

Although a single embodiment of the invention has been described in the above detailed description, it will be understood that the invention is not limited to the embodiment developed herein, but is capable of numerous rearrangements, modifications, substitutions of parts and elements without departing from the spirit and scope of the invention.

The foregoing description comprises illustrative embodiments of the present invention. Having thus described exemplary embodiments of the present invention, it should be noted by those skilled in the art that the within disclosures are exemplary only, and that various other alternatives, adaptations, and modifications may be made within the scope of the present invention. Merely listing or numbering the steps of a method in a certain order does not constitute any limitation on the order of the steps of that method. Many modifications and other embodiments of the invention will come to mind to one skilled in the art to which this invention pertains having the benefit of the teachings presented in the foregoing descriptions. Although specific terms may be employed herein, they are used only in generic and descriptive sense and not for purposes of limitation. Accordingly, the present invention is not limited to the specific embodiments illustrated herein.

What is claimed is:

1. A nutrient composition comprising:

(I) organic intact pea proteins;

(II) one or more fatty acids comprising a ratio of omega 6 to omega 3 from 3:1 to 4:1; and (III) brown rice syrup solids, wherein said one or more fatty acids comprise organic high linoleic sunflower oil, wherein said nutrient composition is free of an allergen, wherein the organic intact pea proteins comprise 100 wt % of a total protein concentration of the nutrient composition, and wherein the nutrient composition is a liquid composition.

2. The nutrient composition of claim 1, wherein the organic intact pea proteins comprise from 5.50 wt % to 6.20 wt % of the nutrient composition.

3. The nutrient composition of claim 1, further comprising a blend of phytochemical extracts derived from one or more fruits, vegetables, herbs and spices.

4. The nutrient composition of claim 1, further comprising rosemary extract.

5. The nutrient composition of claim 3, wherein the blend of phytochemical extracts is derived from one or more of broccoli sprouts, camu camu, tomato, acai, turmeric, garlic, basil, oregano, cinnamon, elderberry, chokeberry, raspberry, spinach, kale, brussels sprouts, extracts of green *arabica* coffee bean, green tea, onion, apple, acerola, Japanese pagoda tree, blackcurrant, blueberry, or bilberry.

6. The nutrient composition of claim 3, wherein the blend of phytochemical extracts comprises from 0.01 wt % to 0.03 wt % of the nutrient composition.

7. The nutrient composition of claim 1, wherein the one or more fatty acids further comprise organic medium chain triglycerides.

8. The nutrient composition of claim 7, wherein the medium chain triglycerides comprise from 1.00 wt % to 1.80 wt % of the nutrient composition.

9. The nutrient composition of claim 1, wherein the one or more fatty acids further comprise organic sunflower lecithin and organic flax seed oil.

10. The nutrient composition of claim 9, wherein the organic sunflower lecithin comprises from 0.05 wt % to 0.10 wt % of the nutrient composition.

11. The nutrient composition of claim 1, further comprising *vanilla* plant extract.

12. The nutrient composition of claim 1, further comprising a vitamin and mineral blend.

13. The nutrient composition of claim 12, wherein the vitamin and mineral blend comprises one or more of a vitamin, mineral, and amino acid, comprising dicalcium phosphate, potassium chloride, magnesium chloride, calcium carbonate, choline bitartrate, sodium ascorbate, trisodium citrate, potassium citrate, L-cysteine, taurine, L-carnitine, inositol, L-tryptophan, DLalpha-tocopheryl acetate, niacinamide, zinc oxide, ferric orthophosphate, calcium pantothenate, pyridoxine hydrochloride, copper sulfate, magnesium sulfate, riboflavin, thiamine hydrochloride, vitamin A palmitate, beta carotene, folic acid, biotin, chromium picolinate, phytonadione, sodium molybdate, sodium selenite, potassium iodide, vitamin D2, or vitamin B12.

14. The nutrient composition of claim 12, wherein the vitamin and mineral blend comprises from 0.80 wt % to 0.95 wt % of the nutrient composition.

15. The nutrient composition of claim 1, further comprising a prebiotic fiber comprising inulin derived from agave.

16. The nutrient composition of claim 15, wherein the prebiotic fiber comprises from 0.95 wt % to 1.14 wt % of the nutrient composition.

17. The nutrient composition of claim 1, further comprising one or more of organic agave syrup, alkalized cocoa, organic *quinoa* flour, organic *vanilla* flavor, or organic milled chia.

18. The nutrient composition of claim 1, wherein the brown rice syrup solids comprise from 4.00 wt % to 10.00 wt % of the nutrient composition.

19. The nutrient composition of claim 1, further comprising organic agave syrup.

20. The nutrient composition of claim 19, wherein the organic agave syrup comprises from 2.85 wt % to 7 wt % of the nutrient composition.

21. The nutrient composition of claim 1, wherein the nutrient composition has a lower glycemic index than an otherwise similar nutrient composition comprising table sugar or high fructose corn syrup.

22. The nutrient composition of claim 1, further comprising potassium citrate.

23. The nutrient composition of claim 4, wherein the rosemary extract comprises from 0.01 wt % to 0.05 wt % of the nutrient composition.

24. The nutrient composition of claim 13, wherein the one or more amino acid comprises L-cysteine, L-carnitine, L-tryptophan, or taurine.

25. The nutrient composition of claim 1, wherein the organic high linoleic sunflower oil comprises from 1.5 wt % to 1.75 wt % of the nutrient composition.

26. The nutrient composition of claim 1, wherein the organic high linoleic sunflower oil comprises from 1.5 wt % to 1.75 wt % of the nutrient composition, and wherein the nutrient composition further comprises rosemary extract in an amount of from 0.01 wt % to 0.05 wt % of the nutrient composition.

27. The nutrient composition of claim 9, wherein the one or more fatty acids comprise organic flax seed oil, wherein the flax seed oil comprises from 0.48 wt % to 0.8 wt % of the nutrient composition.

28. The nutrient composition of claim 7, wherein the organic medium chain triglycerides comprise medium chain triglycerides from organic coconut.

29. The nutrient composition of claim 1, wherein the allergen comprises milk, wheat, soybeans, eggs, peanuts, tree nuts, fish, shellfish, or corn.

30. The nutrient composition of claim 1, further comprising purified water.

31. The nutrient composition of claim 1, wherein the nutrient composition is disposed in an aseptic package.

32. The nutrient composition of claim 1, wherein the nutrient composition is aseptic.

33. The nutrient composition of claim 1, wherein the nutrient composition is shelf stable for at least 6 months.

34. The nutrient composition of claim 1, wherein the nutrient composition fulfills energy requirements of a consumer of the nutrient composition.

35. The nutrient composition of claim 1, wherein the nutrient composition comprises a full amino acid profile comprising histidine, isoleucine, leucine, lysine, methionine, phenylalanine, threonine, tryptophan, and valine.

36. A nutrient composition comprising:

(i) organic intact pea protein at a concentration from 5.5 wt % to 6.2 wt %, wherein the organic intact pea protein comprises 100 wt % of a total protein concentration of the nutrient composition;

(ii) organic brown rice syrup solids at a concentration from 4 wt % to 10 wt % of the nutrient composition;

(iii) organic agave inulin at a concentration from 0.95 wt % to 1.14 wt % of the nutrient composition;

(iv) organic agave syrup at a concentration from 2.85 wt % to 7 wt % of the nutrient composition;

(v) organic high linoleic sunflower oil at a concentration from 1.5 wt % to 1.75 wt % of the nutrient composition;

(vi) organic flax seed oil at a concentration from 0.48 wt % to 0.8 wt % of the nutrient composition;

(vii) organic sunflower lecithin at a concentration from 0.05 wt % to 0.1 wt % of the nutrient composition;

(viii) organic medium chain triglycerides at a concentration from 1 wt % to 1.8 wt % of the nutrient composition;

(ix) a blend of vitamin and minerals at a concentration from 0.8 wt % to 0.95 wt % of the nutrient composition; and (x) one or more phytochemical extracts at a concentration from 0.01 wt % to 0.05 wt % of the nutrient composition, wherein said nutrient composition is free of an allergen, wherein the composition comprises a ratio of omega 6 fatty acids to omega 3 fatty acids from 3:1 to 4:1, and wherein the nutrient composition is a liquid composition.

37. The nutrient composition of claim 36, wherein the blend of vitamin and minerals comprises one or more of a vitamin, mineral, and amino acid, comprising dicalcium phosphate, potassium chloride, magnesium chloride, calcium carbonate, choline bitartrate, sodium ascorbate, trisodium citrate, potassium citrate, L-cysteine, taurine, L-carnitine, inositol, L-tryptophan, DLalpha-tocopheryl acetate, niacinamide, zinc oxide, ferric orthophosphate, calcium pantothenate, pyridoxine hydrochloride, copper sulfate, magnesium sulfate, riboflavin, thiamine hydrochloride, vitamin A palmitate, beta carotene, folic acid, biotin, chromium picolinate, phytonadione, sodium molybdate, sodium selenite, potassium iodide, vitamin D2, or vitamin B12.

38. The nutrient composition of claim 36, wherein the blend of phytochemical extracts is derived from one or more of broccoli sprouts, camu camu, tomato, acai, turmeric, garlic, basil, oregano, cinnamon, elderberry, chokeberry, raspberry, spinach, kale, brussels sprouts, extracts of green *arabica* coffee bean, green tea, onion, apple, acerola, Japanese pagoda tree, blackcurrant, blueberry, or bilberry.

* * * * *